United States Patent [19]

Hjertman et al.

[11] Patent Number: 5,417,662

[45] Date of Patent: May 23, 1995

[54] INJECTION NEEDLE ARRANGEMENT

[75] Inventors: Birger Hjertman, Vällingby; Otto Westphal, Göteborg, both of Sweden

[73] Assignee: Pharmacia AB, Sweden

[21] Appl. No.: 50,144

[22] PCT Filed: Aug. 31, 1992

[86] PCT No.: PCT/SE92/00596

§ 371 Date: May 3, 1993

§ 102(e) Date: May 3, 1993

[87] PCT Pub. No.: WO93/05835

PCT Pub. Date: Apr. 1, 1993

[30] Foreign Application Priority Data

Sep. 13, 1991 [SE] Sweden ................... 9102652

[51] Int. Cl.⁶ ................. A61M 5/00; A61M 5/32
[52] U.S. Cl. ......................... 604/117; 604/198
[58] Field of Search .......... 604/117, 192, 198

[56] References Cited

U.S. PATENT DOCUMENTS

| 2,674,246 | 4/1954 | Bower | 604/198 |
| 2,876,770 | 3/1959 | White | 604/198 |
| 4,373,526 | 2/1983 | Kling | 604/117 |
| 4,416,663 | 11/1983 | Hall | 604/198 |
| 4,507,118 | 3/1985 | Dent | 604/198 |
| 4,955,868 | 9/1990 | Klein | 604/198 |

FOREIGN PATENT DOCUMENTS

| 6366173 | 6/1975 | Australia . |  |
| 2079607 | 1/1982 | United Kingdom | 604/198 |

*Primary Examiner*—John G. Weiss
*Attorney, Agent, or Firm*—Pollock, Vande Sande & Priddy

[57] ABSTRACT

A device for limiting the penetration of an injection needle when an injection is administered from an injection apparatus comprises an exterior sleeve (1) arranged around the front part of the injection apparatus (2). In its foremost position, the sleeve (1) surrounds the needle (8) completely, and it may be displaced rearwards while overcoming a spring force (6), to expose the needle (8).

4 Claims, 2 Drawing Sheets

INJECTION NEEDLE ARRANGEMENT

TECHNICAL FIELD

The present invention refers to the field of hypodermic injections, and more particularly to an arrangement of injection needles or cannulas. Especially, the invention refers to a device for regulating the penetration depth of an injection needle.

DESCRIPTION OF BACKGROUND ART

When an injectable preparation is to be administered to a patient by means of a hypodermic injection, it is often important that the injection is given at a correct location below the surface of the patient's skin. This means that it is necessary to administer the injection in such a way that the injectable preparation is expelled at a correct depth under the surface of the skin. If the injected preparation is administered at an incorrect depth, i.e. too superficial or too deep, this may mean that the injection will have an inferior effect, or have unexpected side effects. In both cases, this may lead to serious consequences for the patient.

This is not an important problem when injections are administered by a trained physician or nurse, such as in a hospital. However, in recent years, a number of devices have been developed, by means of which a patient can administer injections to himself, such as in the ambulatory treatment of diabetes with insulin. These devices usually comprise a holder for a standard cartridge of an injectable preparation, and a dosing device, which can be set to measure and administer a predetermined dose of the preparation. An injection needle or cannula is attached to one end of the cartridge to establish a connection with the interior of said cartridge, and by means of the dosing device, the set dose of the preparation is expelled from the cartridge through the needle. These injection devices are very practical for the patient, but as the patient usually does not have any medical training, there is a risk that he will insert the needle to an incorrect depth, so that the injection is not given at the correct location under the skin.

Another drawback of the known injection devices for self-administering is that the attached injection needle is fully exposed. Many persons find it very unpleasant to administer injections to themselves in this way. There seems to be a psychological block in many persons against penetrating one's own skin with a fully exposed needle. Because of this, there have for certain applications been developed auto-injectors, where a concealed needle is made to penetrate the patient's skin when a spring arrangement is released. Such arrangements, however, are complicated and expensive, and are not suitable for self-injection devices where a number of injections are to be administered from one cartridge.

SUMMARY OF INVENTION

By the device of the present invention, the drawbacks mentioned above may now be eliminated. Through this device, an injection needle is prevented from penetrating to an incorrect depth when an injection is administered, and the needle itself may be essentially concealed before, during and after the administration process. Because of the increased surface resting against the skin, an improved stability is also achieved against an involuntary movement during the injection.

In accordance with the invention, there is provided a device for limiting the penetration of the needle of an injection apparatus when an injection is administered, said device comprising an axially displaceable, tubular exterior sleeve arranged around the front part of said injection apparatus, wherein the sleeve in its foremost position surrounds the needle over its whole length, and, while overcoming a spring force, is displaceable axially rearwards to expose a predetermined length of the needle.

In a preferred embodiment, the sleeve is provided with stopping means, which prevent the sleeve from being displaced rearwards by more than a predetermined distance.

In a further preferred embodiment, the device is provided with fastening means to attach the sleeve releasably to the front part of said injection apparatus.

BRIEF DESCRIPTION OF DRAWINGS

The invention is further illustrated by the accompanying drawing. In the drawing.

DESCRIPTION OF BEST AND VARIOUS MODES FOR CARRYING OUT INVENTION

Figure 1:
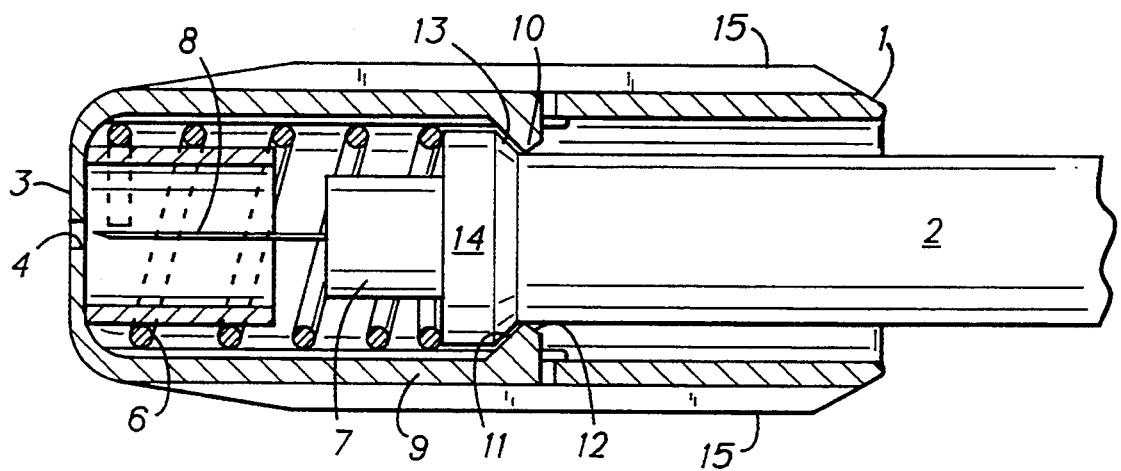
FIG. 1 shows a partly sectional view of a device according to the invention attached to the front end of an injection apparatus and with the needle surrounded by the device.

FIG. 1 shows a sectional view of the tubular sleeve 1 arranged around the front part of the barrel 2 of an injection apparatus. At its front end, the sleeve 1 is closed by an endwall 3, which has a central hole 4. Inside the exterior sleeve 1, at its front end, is arranged an interior tubular sleeve 5, which extends rearwards for a predetermined length. In a spacing between the interior wall of the exterior sleeve 1 and the exterior wall of the interior sleeve 5 is arranged a helical spring 6, which extends between the inside of the front end wall 3 and the front end of the barrel 2 of the injection apparatus, and which strives to push the sleeve 1 and the injection apparatus 2 apart from each other.

The injection apparatus is largely of a conventional design, and comprises a barrel 2, which at its front end is provided with means, such as a threaded cap 7, for removably attaching an injection needle 8. This needle or cannula is in liquid connection with a container inside the injection apparatus for the preparation to be injected. At its front end, the injection apparatus is also provided with means for releasably connecting the exterior sleeve 1 with the barrel 2. These means are the only modification necessary in an otherwise conventional injection apparatus, and will be described in more detail below. In all other respects, the injection apparatus is of a conventional design and usually comprises a metering and dosing mechanism. A number of such injection apparatuses are commercially available and may easily be modified to be adapted to the device of the invention.

One embodiment of the means for releasably connecting the exterior sleeve 1 to the barrel 2 of the injection apparatus is shown in the drawing. These means comprise flexible tongues 9, which are arranged in the wall of the exterior sleeve 1 and are provided with projections 10. These projections have forward and rearward facing surfaces 11 and 12, respectively, which are inclined towards the interior wall of the sleeve 1, and the forward facing surface 11 matches the rearward facing surface 13 of an annular projection 14 arranged at the forward end of the barrel 2 around the cylindrical surface of said barrel. Through the action of the helical spring 6 acting on the front end of the barrel 2 of the injection apparatus, said apparatus is urged rearwards in relation to the sleeve 1, such that the inclined surface 13 rests against the forward facing surface 11 of each projection 10. The force of the spring 6, however, is not sufficient to overcome the spring force of the flexible tongues 9 and push them outwards by its action on the inclined surfaces 11.

Usually at least two flexible tongues 9 with projections 10 are arranged in the wall of the exterior sleeve 1, as is shown in the drawing. These tongues are preferably arranged with a uniform spacing around the circumference of the sleeve 1. It is furthermore to be noted that in the drawing, the details of this connecting arrangement are shown in an exaggerated size, to show its function more clearly.

On each side of the flexible tongues 9 may also be arranged longitudinal ridges 15 in the outer wall of the exterior sleeve 1. These ridges protect the tongues 9 from being disturbed in their function as releasable connecting devices.

As can be seen in FIG. 1, the needle 8 of the injection apparatus is completely surrounded and concealed inside the exterior sleeve 1, and is thereby also protected against mechanical damage.

Figure 2:
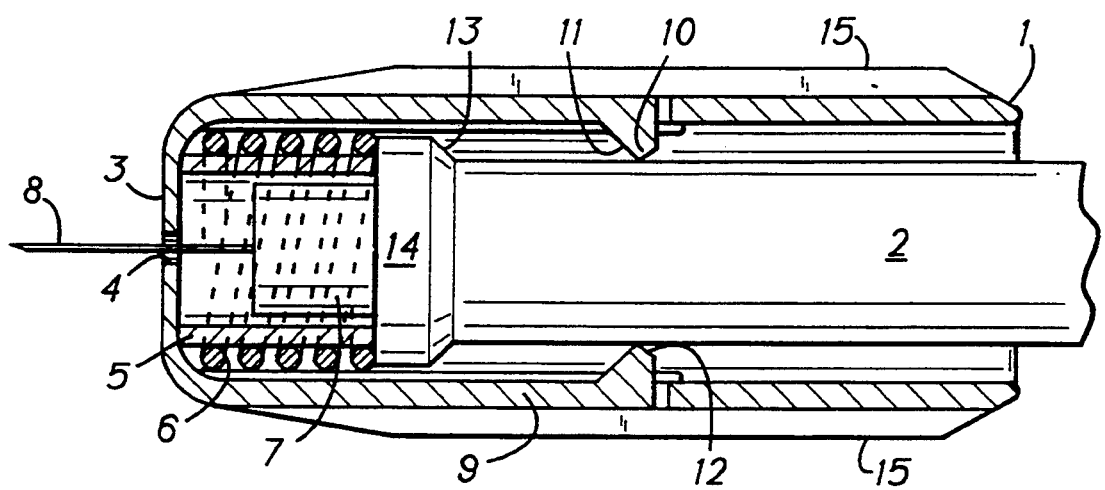
FIG. 2 shows a similar view like the one in FIG. 1, but with the device in its rear position and with the needle exposed.

FIG. 2 shows the device of the invention in its position when an injection is to be administered. The exterior sleeve 1 has been displaced rearwards in relation to the injection apparatus 2, overcoming the force of the helical spring 6. The rearward displacement is limited by the interior sleeve 5 when the front face of the barrel 2 of the injection apparatus abuts against the rear end of said interior sleeve 5. The needle 8, which is arranged coaxially with the hole 4 in the front end wall 3 of the exterior sleeve 1, will now protrude through said hole 4 in said end wall 3. The distance that the needle 8 protrudes from the end wall 3, and which determines the depth of the injection, is governed by the length of the interior sleeve 5, such that a shorter interior sleeve 5 will mean that the exterior sleeve 1 may be displaced further rearwards, exposing more of the needle 8.

The flexible tongues 9 with their projections 10 will not affect the rearward displacement of the exterior sleeve 1, as the edges of the projections 10 will only slide along the surface of the barrel 2 of the injection apparatus.

Figure 3:
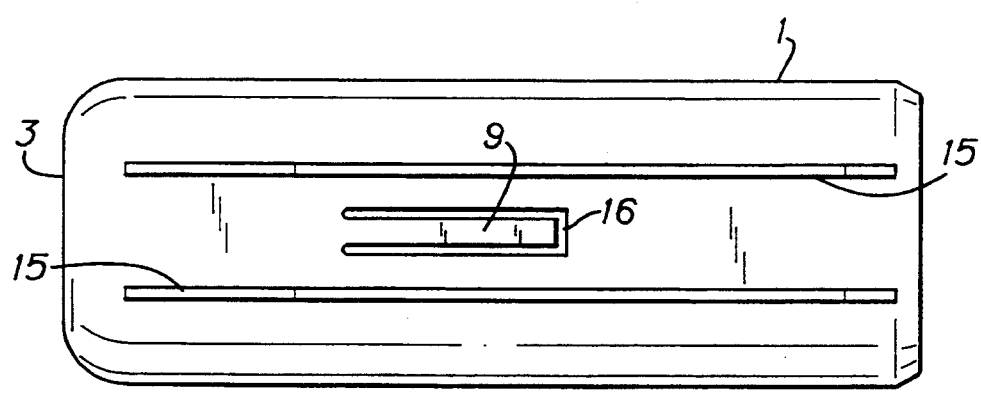
FIG. 3 shows a plane view of the device of the invention, further illustrating an embodiment of the fastening means. In the figures, like parts have the same reference numbers.

FIG. 3 shows a plane view of the device of the invention, and primarily serves to show the arrangement of the flexible tongues 9. It can here be seen that each tongue 9 is formed by the wall material of the exterior sleeve 1 when an U-shaped aperture 16 is taken up through said wall. The flexible spring properties of the tongues 9 are determined by the dimensions of the tongues and by the elastic properties of the material used for the exterior sleeve 1. These parameters can easily be determined by those skilled in the art, by simple tests.

Expressed in general terms, the flexible tongues 9 thus serve as a snap-locking device arranged in the exterior sleeve 1, which cooperates with a corresponding device which has been arranged at the front end of the injection apparatus.

The ridges 15 on each side of the tongue 9 are also shown in FIG. 3.

It is to be noted that the arrangement for releasably attaching the device of the invention to the barrel of the injection apparatus is only one example of a number of possible embodiments. Thus, instead of having an annular projection 14 at its front end, the barrel of the injection apparatus may be provided with an annular groove around its front end, such that the projections 10 of the flexible tongues rest in this groove and thereby lock the device and the injection apparatus releasably together. Another embodiment may be in the form of a bayonet lock of various types. What is important is that the exterior sleeve 1 of the device should be securely but releasably locked to the barrel 2 of the injection apparatus, and that a movement of the sleeve 1 rearwards from the locking position should be possible.

The function of the device of the invention is as follows:

Firstly, the injection apparatus is made ready in the usual manner for the administration of an injection. This usually comprises charging the apparatus with an injection cartridge, if this has not been done previously, and attaching a fresh injection needle or cannula to the front end of the apparatus by means of the threaded cap 7. In transport and storage, the needle is usually also provided with a protective cap, and this cap should now also be removed.

The injection apparatus is then inserted with its needle end foremost into the exterior sleeve 1 through the open rear end of said sleeve. When the barrel 2 of the injection apparatus has been inserted a certain distance into the sleeve 1, the front face of the annular projection 14 will abut against the rearward-facing surfaces 12 of the projections 10 of the flexible tongues 9, and by further pressure on these inclined surfaces 12, the flexible tongues 9 will be urged outwards in the radial direction. The barrel 2 of the injection apparatus may then be inserted further into the sleeve 1, now also against the force of the helical spring 6. When the projections 10 have passed over the annular projection 12, they will, by the spring action of the flexible tongues 9, snap in behind the annular projection 14, such that the forward-facing inclined surfaces 11 of the projections 10 will now rest against the matching rearward-facing inclined surface 13 of the annular projection 14. The two inclined surfaces 11 and 13 will be pressed against each other by the action of the spring 6. The needle 8 of the injection apparatus 2 will be completely surrounded by the front part of the exterior sleeve 1, and will be aligned with the hole 4 in the front end wall 2 of said sleeve.

When an injection is to be administered, the exterior sleeve 1 is moved rearwards along the barrel 2 of the injection apparatus, against the force of the helical spring 6, until the front face of the annular projection 14 abuts against the rear end of the interior sleeve 5. The needle 8 will now protrude for a predetermined length through the hole 4 in the front end wall 3 of the exterior sleeve 1, and the injection may be administered to a correct depth from the injection apparatus 2, by operating a conventional dosing mechanism included in the injection apparatus.

The injection may be administered to the patient in such a way that the front end wall 2 of the device of the invention is placed in contact with the patient's skin on the site where the injection is to be given, while the needle is still retracted inside the exterior sleeve 1. By moving the injection apparatus 2 forward against the force of the spring 6, the needle 8 is moved out through the hole 4, to pierce the patient's skin, after which the injection is administered by means of the dosing mechanism of the injection apparatus. By this method, the patient will not see the injection needle during the administering process, which many patients regard as unpleasant.

After the injection has been administered, the needle 8 is withdrawn from the patient, and the force of the spring 6 will now urge the exterior sleeve 1 forward, so that the needle will retract into it and will be concealed from view by the patient.

When a new injection is to be administered, a fresh injection needle is usually attached to the injection apparatus. For this, the barrel 2 of the injection apparatus is pulled back from the exterior sleeve 1. The inclined rearward-facing surface 13 of the circular projection 14 will then push against the inclined forward-facing surface 11 of the projections 10 with a sufficient force to urge the projections 10 radially outwards against the spring action of the flexible tongues 9, so that the injection apparatus is freed from the exterior sleeve 1. The injection apparatus may then be readied for a new injection, as described above.

During the administering process and the handling before and after the administering, the needle of the injection apparatus will not get into any physical contact with any part of the device of the invention. It will therefore not be necessary to sterilize the device between the injections. However, if a sterilizing should be necessary for some reason, this can easily be carried out, for instance by autoclaving at a high temperature, as the device does not contain any parts which are adversely affected by such a sterilizing process.

The device of the invention is usually manufactured from a plastic material which can be worked to the desired shape and which can stand the temperatures used in heat sterilizing. The spring is usually made of stainless steel. For a person skilled in the art and having knowledge about the design of the device, there are no difficulties in selecting suitable materials and processes for the manufacture of devices according to the invention.

By the use of a device in accordance with the invention, a number of advantages are obtained:

The injection needle is concealed and is protected from mechanical influences before and after administration of the injection.

The penetration of the injection needle is controlled to a correct depth below the surface of the skin.

The penetration depth of the needle may be varied by using internal sleeves of different length, without changing any other part of the device.

The device can be used a number of times without having to be sterilized between the injections.

A needle which has become unsterile after the injection is protected by the device.

The injection apparatus to be used with the device can be of a conventional design, and will only have to be slightly modified.

The device does not have to be discarded when a disposable injection apparatus has been used up, but can be used with a subsequent injection apparatus as many times as desired.

Because of the increased surface resting against the skin, and improved stability is also achieved against an involuntary movement during the injection.

In the present specification and drawing, the device of the invention has been described with special reference to the embodiment shown in the drawing. A person skilled in the art will realise, however, that this embodiment is only an example, and that the scope of the invention is only limited by the appended claims.

We claim:

1. A device for limiting the penetration of a needle of an injection apparatus when an injection is administered, comprising:
    an axially displaceable, tubular exterior sleeve arranged around a front part of said apparatus, said sleeve in its foremost position surrounding a needle over its entire length, and, while overcoming a spring force effected by a helical spring arranged inside the exterior sleeve, is displaceable axially rearwards to expose a first predetermined length of a needle;
    stopping means for preventing the exterior sleeve from being displaced backwards for more than a second predetermined length, wherein said stopping means comprises an interior sleeve that is arranged inside the exterior sleeve and extends from the front end of said exterior sleeve rearwards by said second predetermined length; and
    fastening means for releasably attaching the exterior sleeve to the front part of the injection apparatus, wherein said fastening means consists of a snap-locking device arranged in said exterior sleeve, which releasably cooperates with a corresponding device, and which is arranged at the front part of said injection apparatus.

2. The device of claim 1 wherein fastening means is slidable.

3. The device of claim 1 wherein a major part of the helical spring is positioned rearwards of a point for attachment of the needle of a injection apparatus when the injection is administered.

4. The device of claim 2 wherein a major part of the helical spring is positioned rearwards of a point for attachment of a needle of the injection apparatus when the injection is administered.

* * * * *